United States Patent [19]
Strizhov et al.

[11] Patent Number: 6,110,668
[45] Date of Patent: Aug. 29, 2000

[54] GENE SYNTHESIS METHOD

[75] Inventors: Nicolai Strizhov; Csaba Koncz; Jeff Schell, all of Köln, Germany

[73] Assignee: Max-Planck-Gesellschaft zur Forderung der Wissenschaften E.V., Berlin, Germany

[21] Appl. No.: 08/769,802

[22] Filed: Dec. 20, 1996

Related U.S. Application Data
[60] Provisional application No. 60/027,896, Oct. 7, 1996.

[51] Int. Cl.[7] .................. C12Q 1/68; C12P 19/34
[52] U.S. Cl. .................. 435/6; 435/91.1; 435/91.2; 536/25.3
[58] Field of Search .................. 435/6, 5, 91.1, 435/91.2, 4; 536/23.1, 24.3, 24.33, 25.3

[56] References Cited

U.S. PATENT DOCUMENTS

| | | |
|---|---|---|
| 4,652,639 | 3/1987 | Stabinsky . |
| 4,888,286 | 12/1989 | Crea . |
| 5,158,877 | 10/1992 | Edwards et al. . |
| 5,367,066 | 11/1994 | Urdea et al. ............... 536/24.3 |
| 5,380,831 | 1/1995 | Adang et al. . |
| 5,503,995 | 4/1996 | Khudyakov et al. . |
| 5,506,137 | 4/1996 | Mathur et al. ............... 435/252.3 |
| 5,547,843 | 8/1996 | Studier et al. ............... 435/6 |
| 5,593,840 | 1/1997 | Bhatnagar et al. ............... 435/6 |

OTHER PUBLICATIONS

Wiedmann et al., Appl. Environ. Microbiol. 59(8), 2743–2745, 1993.

Weisberg, Edward P. eet al., "*Simultaneous Mutagenesis of Multiple Sites: Application of the Ligase Chain Reaction Using PCR Products Instead of Oligonucleotides*", Bio-Feedback, vol. 15, No. 1, (1993)pp. 68–75.

Kozak, Marilyn, "*Downstream Secondary Structure Facilitates Recognition of Initiator Codons by Eukaryotic Ribosomes*", Proc. Natl. Acad. Sci USA, Nov. 1990, vol. 87, pp. 8301–8305.

*Primary Examiner*—Kenneth R. Horlick
*Attorney, Agent, or Firm*—Foley & Lardner

[57] ABSTRACT

A method of gene synthesis is disclosed. The gene synthesis method permits the codons of [m] natural gene to be changed to allow preferential transcription and translation of the synthetic gene in transgenic organisms. The method utilizes a combination of enzymatic and chemical synthesis of DNA and significantly reduces the cost, time and number of steps required for construction of synthetic genes.

8 Claims, 3 Drawing Sheets

1: AUTOMATED SYNTHESIS OF 5'-PHOSPHORYLATED OLIGONUCLEOTIDES

2: TEMPLATE DIRECTED LIGATION OF OLIGONUCLEOTIDES ANNEALED TO A PARTIALLY COMPLEMENTARY SINGLE-STRANDED DNA CARRYING WILD-TYPE GENE SEQUENCE

3: SELECTIVE PCR AMPLIFICATION OF SYNTHETIC DNA STRAND

FIG. 1

```
              -    AT    ATACA       T  AAG       A           C  A
     GGATCCACCATGGAGGAGAACAATCAGAACCAGTGTATCCCTTACAATTGTCTTTCTAATCCTGAAGAAGTTCTTTTGGATGGAGAAAGGATCTCAACTG
   1 ---------+---------+---------+---------+---------+---------+---------+---------+---------+---------+
                M  E  E  N  N  Q  N  Q  C  I  P  Y  N  C  L  S  N  P  E  E  V  L  L  D  G  E  R  I  S  T  G

T   ▼  TT  G         TC  A         A  G      TTA     TAATTA
     GTAACTCATCAATTGACATCTCTCTCTCACTTGTTCAGTTCTTGGTTTCTAACTTTGTGCCAGGAGGAGGATTCCTTGTTGGACTTATCGACTTCGTTTG
 101 ---------+---------+---------+---------+---------+---------+---------+---------+---------+---------+
         N  S  S  I  D  I  S  L  S  L  V  Q  F  L  V  S  N  F  V  P  G  G  G  F  L  V  G  L  I  D  F  V  W

A   C              ▼      AAAT    ATATT        A    AT
     GGGAATCGTTGGACCTTCTCAATGGGATGCATTTCTCGTTCAGATCGAACAGCTCATCAACGAAAGAATCGCTGAGTTCGCTAGGAATGCTGCTATTGCT
 201 ---------+---------+---------+---------+---------+---------+---------+---------+---------+---------+
         G  I  V  G  P  S  Q  W  D  A  F  L  V  Q  I  E  Q  L  I  N  E  R  I  A  E  F  A  R  N  A  A  I  A

TT A   TA    T  TAT  A  TA    ▼          TT                  AT
     AACCTTGAAGGACTTGGAAACAACTTCAACATCTACGTGGAGGCATTCAAGGAATGGGAAGAAGATCCTAACAACCCAGCAACCAGGACCAGAGTGATCG
 301 ---------+---------+---------+---------+---------+---------+---------+---------+---------+---------+
         N  L  E  G  L  G  N  N  F  N  I  Y  V  E  A  F  K  E  W  E  E  D  P  N  N  P  A  T  R  T  V  I  D

CCT  A    GA         TCG  CAT       ▼    AC TAC  T      G
     ATAGGTTCCGTATCCTTGATGGACTTCTTGAAAGGGACATTCCTAGCTTTAGGATCTCTGGATTTGAAGTTCCACTTCTCTCTGTTTACGCTCAAGCTGC
 401 ---------+---------+---------+---------+---------+---------+---------+---------+---------+---------+
         R  F  R  I  L  D  G  L  L  E  R  D  I  P  S  F  R  I  S  G  F  E  V  P  L  L  S  V  Y  A  Q  A  A

C   G   A    ATA      ATT           ▼      GATCTA    TT    AT
     TAATCTCCATCTTGCTATCCTTAGAGATTCTGTGATCTTCGGAGAAAGATGGGGATTGACAACCATCAACGTGAACGAGAACTACAACAGACTCATCAGG
 501 ---------+---------+---------+---------+---------+---------+---------+---------+---------+---------+
         N  L  H  L  A  I  L  R  D  S  V  I  F  G  E  R  W  G  L  T  T  I  N  V  N  E  N  Y  N  R  L  I  R

TT    AT         ATGTTG TAT TTAGA   G      ▼      A   TTT
     CACATCGATGAGTACGCTGATCACTGTGCTAACACTTACAACCGTGGACTCAACAACCTTCCTAAGTCTACCTATCAAGATTGGATCACATACAACCGAC
 601 ---------+---------+---------+---------+---------+---------+---------+---------+---------+---------+
         H  I  D  E  Y  A  D  H  C  A  N  T  Y  N  R  G  L  N  N  L  P  K  S  T  Y  Q  D  W  I  T  Y  N  R  L

AC    TA     ATA      C                                     ▼HincII A
     TTAGGAGAGACCTTACATTGACTGTTCTTGATATCGCTGCTTTCTTTCCAAACTATGACAATAGGAGATATCCAATTCAGCCAGTTGGTCAACTTACAAG
 701 ---------+---------+---------+---------+---------+---------+---------+---------+---------+---------+
         R  R  D  L  T  L  T  V  L  D  I  A  A  F  F  P  N  Y  D  N  R  R  Y  P  I  Q  P  V  G  Q  L  T  R T   G     TAT.TTT    TA    A    ATA   T  T            ▼      T
     GGAAGTTTACACTGACCCACTCATCAACTTCAACCCACAGCTTCAGTCTGTTGCTCAGCTTCCTACCTTCAACGTTATGGAGAGCAGCGCAATCAGAAAT
 801 ---------+---------+---------+---------+---------+---------+---------+---------+---------+---------+
         E  V  Y  T  D  P  L  I  N  F  N  P  Q  L  Q  S  V  A  Q  L  P  T  F  N  V  M  E  S  S  A  I  R  N TTATTA   TT          G           CTTT              AA
     CCTCACCTCTTCGACATCTTGAACAACCTTACAATCTTTACCGATTGGTTTAGTGTTGGACGTAACTTCTACTGGGGAGGACATCGAGTGATCTCTAGCC
 901 ---------+---------+---------+---------+---------+---------+---------+---------+---------+---------+
         P  H  L  F  D  I  L  N  N  L  T  I  F  T  D  W  F  S  V  G  R  N  F  Y  W  G  G  H  R  V  I  S  S  L TA   ▼     A       AT       G             CT   TT   GAT     T
     TCATCGGAGGTGGTAACATCACATCTCCTATCTACGGAAGAGAGGCTAACCAGGAGCCTCCAAGATCATTCACTTTCAACGGACCTGTGTTCAGGACTCT
1001 ---------+---------+---------+---------+---------+---------+---------+---------+---------+---------+
         I  G  G  G  N  I  T  S  P  I  Y  G  R  E  A  N  Q  E  P  P  R  S  F  T  F  N  G  P  V  F  R  T  L
```

FIG. 2A

```
            A      TA TATA   ▼        G     TTA               AAT           T
        TTCAAATCCTACTCTTCGACTTCTTCAGCAACCTTGGCCAGCTCCACCATTCAACCTTCGTGGTGTTGAAGGAGTTGAGTTCTCTACACCTACAAACAGC
1101    ----------+---------+---------+---------+---------+---------+---------+---------+---------+---------+
          S  N  P  T  L  R  L  L  Q  Q  P  W  P  A  P  P  F  N  L  R  G  V  E  G  V  E  F  S  T  P  T  N  S

T G   A     ▼   G        TA     TAG      TT          C        T          TA
        TTCACCTATCGTGGAAGAGGTACTGTTGATTCTCTTACTGAACTTCCACCTGAGGACAACAGTGTGCCACCTCGTGAAGGATACAGTCATCGTCTTTGTC
1201    ----------+---------+---------+---------+---------+---------+---------+---------+---------+---------+
          F  T  Y  R  G  R  G  T  V  D  S  L  T  E  L  P  P  E  D  N  S  V  P  P  R  E  G  Y  S  H  R  L  C  H

T T      ▼ BglII ▼       TT A         AAT       G           ▼           A T
        ATGCAACCTTCGTTCAAAGATCTGGAACACCTTTCCTTACAACTGGTGTTGTGTTCTCTTGGACTCATCGTAGTGCAACTCTTACCAACACAATTGATCC
1301    ----------+---------+---------+---------+---------+---------+---------+---------+---------+---------+
          A  T  F  V  Q  R  S  G  T  P  F  L  T  T  G  V  V  F  S  W  T  H  R  S  A  T  L  T  N  I  D  P

ATTAA  TA         T         GC     C         ▼       T         G
        AGAGAGGATCAACCAGATCCCTCTTGTGAAAGGATTCAGAGTTTGGGGAGGAACCTCTGTGATTACAGGACCAGGATTCACAGGAGGTGATATCCTTCGA
1401    ----------+---------+---------+---------+---------+---------+---------+---------+---------+---------+
          E  R  I  N  Q  I  P  L  V  K  G  F  R  V  W  G  G  T  S  V  I  T  G  P  G  F  T  G  G  D  I  L  R

T       TT A    A    C TTT      T         ▼     TA          C
        AGAAACACCTTTGGTGACTTCGTTTCTCTTCAAGTGAACATCAACTCACCAATCACCCAAAGATACCGTCTTAGATTTCGTTACGCTTCTAGTAGGGATG
1501    ----------+---------+---------+---------+---------+---------+---------+---------+---------+---------+
          R  N  T  F  G  D  F  V  S  L  Q  V  N  I  N  S  P  I  T  Q  R  Y  R  L  R  F  R  Y  A  S  S  R  D  A

A  ATA      G    C       ▼       C        AT               AAG     T
        CACGAGTTATCGTTCTTACAGGAGCTGCATCTACAGGAGTGGGAGGTCAAGTTAGTGTGAACATGCCTCTTCAGAAAACTATGGAGATCGGAGAGAACCT
1601    ----------+---------+---------+---------+---------+---------+---------+---------+---------+---------+
          R  V  I  V  L  T  G  A  A  S  T  G  V  G  G  Q  V  S  V  N  M  P  L  Q  K  T  M  E  I  G  E  N  L

A  ▼     T    T   TT        T      T          TATGA             A T
        CACATCTAGAACATTCAGATACACCGACTTCAGTAATCCTTTCTCATTCAGAGCTAATCCAGACATCATCGGTATCAGTGAACAACCTCTCTTCGGTGCA
1701    ----------+---------+---------+---------+---------+---------+---------+---------+---------+---------+
          T  S  R  T  F  R  Y  T  D  F  S  N  P  F  S  F  R  A  N  P  D  I  I  G  I  S  E  Q  P  L  F  G  A

T       ▼    TATATATTA                          TT A
        GGTTCTATCAGTAGCGGTGAACTTTACATCGACAAGATCGAGATCATCCTTGCAGATGCAACATTTGAAGCAGAATCTGACCTTGAAAGAGCACAAAAGT
1801    ----------+---------+---------+---------+---------+---------+---------+---------+---------+---------+
          G  S  I  S  S  G  E  L  Y  I  D  K  I  E  I  I  L  A  D  A  T  F  E  A  E  S  D  L  E  R  A  Q  K  ·

AGGATCC
1901    ------- 1907
```

FIG. 2B

GENE SYNTHESIS METHOD

This application claims benefit of U.S. Provisional application Ser. No. 60/027,896 filed on Oct. 7, 1996 and incorporated herein by reference.

BACKGROUND OF THE INVENTION

Gene Synthesis Techniques

The present invention relates to a method of gene synthesis and more particularly to a gene synthesis method wherein the codons of a natural gene can be changed to allow optimal transcription and translation of the gene in transgenic organisms which prefer particular codons and other sequences that differ from those of the natural gene.

The degeneracy of the genetic code permits substantial freedom in the choice of codons for any particular amino acid sequence. Transgenic organisms such as plants frequently prefer particular codons which, though they encode the same protein, may differ from the codons in the organism from which the gene was derived. For example, U.S. Pat. No. 5,380,831 to Adang et al., relates to the creation of insect resistant transgenic plants that express the *Bacillus thuringiensis* (Bt) toxin gene. The Bt crystal protein, an insect toxin, is encoded by a full-length gene that is poorly expressed in transgenic plants. In order to improve expression in plants, a synthetic gene encoding the protein containing codons preferred in plants was substituted for the natural sequence. The invention disclosed therein comprised a chemically synthesized gene encoding an insecticidal protein which is frequently equivalent to a native insecticidal protein of Bt. The synthetic gene was designed to be expressed in plants at a level higher than a native Bt gene.

The approach used to assemble the Bt gene in the '831 patent is one of several methods for gene synthesis for genetic engineering manipulation. It consisted of designing an improved nucleotide sequence for the coding region and assembling the gene from a number of short chemically synthesized oligonucleotide segments. The DNA sequence to be synthesized was divided into segments, with lengths that can be synthesized, isolated and purified. The segments were then joined enzymatically to form the synthetic Bt gene.

Disadvantages of the gene synthesis method described in the '831 patent include its speed, costs, and efficiency. The approach is very sensitive to the secondary structure of oligonucleotides (e.g., hairpin loops) which interfere with the assembly. Hence, the approach has low efficiency and is not reliable for construction of long synthetic DNA fragments. Moreover, the method involves numerous steps and requires synthesis of both strands of the DNA. It requires purification of many short (50–70 nt) oligonucleotides by rather laborious and time consuming procedures. Use of T4 DNA ligase requires conventional temperatures (20°–37° C.) during assembly and ligation of oligonucleotides therefore contributing to the sensitivity of the method to secondary DNA structure.

Another approach to gene synthesis is described in U.S. Pat. No. 4,652,639 to Stabinsky. That reference also relates to a method for DNA synthesis wherein the synthetic gene has alternative codons selected on the basis of preferential expression in a projected host organism to be transformed. The method employed involves the ligation of two or more DNA strands although no template is employed. A key disadvantage of the gene synthesis method described in the '639 patent is that it can only be employed to synthesize short genes of about 200 base pairs. It is, however, frequently desirable to create longer genes.

Yet another method for the synthetic assembly of oligonucleotides into long DNA fragments utilizes polymerase to fill in single-stranded gaps in annealed pairs of oligonucleotides. However, after the polymerase reaction, each segment must be cloned, a step which significantly delays the synthesis of long DNA fragments and greatly decreases the efficiency of the approach. Additionally, the approach can be used only for small DNA fragments.

Recently, several PCR based techniques have been developed for construction of synthetic genes, where an assembly of overlapping oligonucleotides is performed by a thermostable DNA polymerase during repeated cycles by melting, anneling and polymerization. Although PCR mediated methods are rather simple and labor saving, they are not free from drawbacks. A key disadvantage of assembly by PCR is that complex mispriming events negatively exert the correctness of a resulting assembled DNA. In addition, the low fidelity of thermostable DNA polymerase influences the reliability of this technology with increased number of PCR steps.

Template Directed Ligation

There is known in the art a ligase mediated method for detecting mutations that exploits the fact that the ends of two single strands of DNA must be exactly aligned for DNA ligase to join them. U.S. Pat. No. 5,547,843 to Studier et al, briefly summarizes a template-directed ligation method wherein two contiguously annealing oligonucleotides are incubated with a template molecule which contains a nucleotide sequence complimentary to the oligonucleotide. The oligonucleotides anneal to form a contiguous duplex structure. The complex is then contacted with a ligase enzyme which joins the adjacent oligonucleotide through a phosphodiester linkage. The only utility suggested in the '843 patent and the prior art in general for template-directed ligation is as a diagnostic method for the detection of point mutations in DNA. Heretofore, there has been no teaching or suggestion in the art of utilizing template directed ligation for the assembly and construction of synthetic genes in a manner which overcomes the above-described disadvantages of prior art techniques.

SUMMARY OF INVENTION

The present invention is a new method for assembly and construction of synthetic genes which are similar but not necessarily identical to a natural gene of interest. The method utilizes a combination of enzymatic and chemical synthesis of DNA and significantly reduces the cost, time and number of steps required for construction of synthetic genes.

In short, chemically synthesized and phosphorylated oligonucleotides of the gene to be created are assembled on a single-stranded partially homologous template DNA derived from the natural or wild-type gene. After annealing, the nicks between adjacent oligonucleotides are closed by a thermostable DNA ligase using repeated cycles of melting, annealing, and ligation. This template directed ligation ("TDL") results in a new single-stranded synthetic DNA product which is subsequently amplified and isolated from the wild type template strand by the polymerase chain reaction (PCR) with short flanking primers that are complementary only to the new synthetic strand. These PCR end-primers contain suitable restriction cleavage sites for cloning of the synthetic double-stranded DNA fragments.

There are many advantages of the "TDL-PCR" gene synthesis method according to the present invention over the above-described prior art approaches. First, only one strand is required to be synthesized thereby reducing the time requirements by about one half. Second, the use of thermostable DNA ligase permits the process to be carried out at higher temperatures which decreases the formation of secondary structures (e.g. hairpin loops) that interfere with the assembly process. Third, because only phosphorylated oligonucleotides will be ligated during repeated TDL cycles there is no need to purify full length oligonucleotides. Fourth, the process involves fewer steps than the prior art approaches thereby increasing efficiency and decreasing the likelihood of errors.

In the TDL-PCR method the PCR is used only in the final step, thus avoiding the assembly of oligonucleotides, in contrast to PCR based methods for gene synthesis described in the preceding section. The gene assembly by ligation of oligonucleotides is preferable to assembly by PCR approach, because no new errors are introduced to the assembled DNA. Indeed, the analysis of the observed errors showed (Example 1) that these originate from chemical oligonucleotide synthesis—a common problem with any gene synthesis technology, and that using the PCR in the final step did not introduce additional errors.

The disclosed TDL-PCR method for gene synthesis represents a general method which may be employed to create a synthetic version of a natural or wild-type gene from any plant or animal or any existing gene as long as the wild-type sequence is known and present. The simplicity of the method allows it to be widely used in areas where the routine re-synthesis of the sequences is required. There is an increasing demand for processes that alter DNA sequences to permit the construction of transgenic organisms. As a result of billions of years of evolution, microorganisms have genes in their genome that are not present in other higher organisms such as plants and vertebrates. Frequently such genes are not suited for expression in eukaryotic organisms and vice- versa. Moreover, even in plants the monocot and the dicot genes differ by expression requirements, and therefore need to be reconstructed to fit different expression patterns.

With the foregoing and other objects, advantages and features of the invention that will become hereinafter apparent, the nature of the invention may be more clearly understood by reference to the following detailed description of the invention, the figures, and the appended claims.

DETAILED DESCRIPTION OF THE INVENTION

Prior to initiating the synthesis process, the sequence of the new gene to be created is designed based on the known sequence of the wild-type gene. If the new gene will be used to transform a plant, then modifications will be made with respect to the plant's preferred codons and to other fortuitous sequences resembling the signals which initiate various processing steps in transcription and translation of the gene. Avoidance of such signals can drastically increase expression of a transgene in plants.

Figure 1:
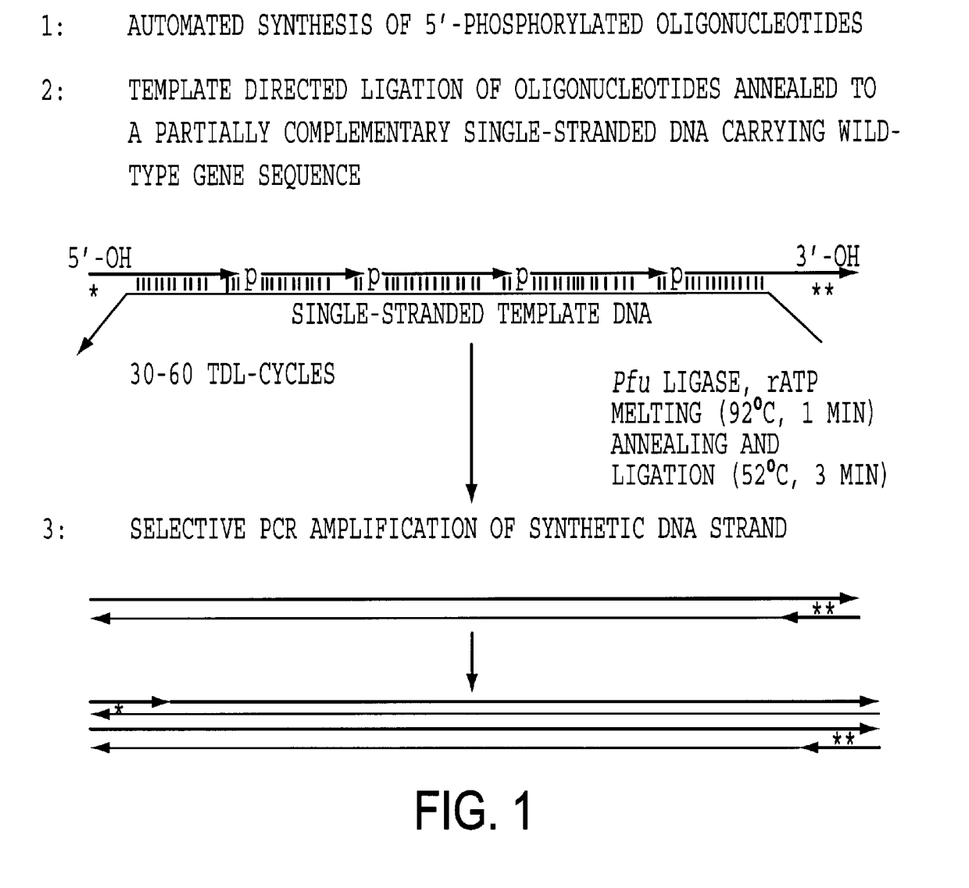
FIG. 1 is a schematic plan for gene synthesis according to the present invention.

Gene synthesis according to the present invention generally comprises three steps which are illustrated schematically in FIG. 1.

During the first step a plurality (e.g. eight) of oligonucleotides, each of a length of between 80–130 bases which collectively comprise the newly designed sequence, are chemically synthesized and phosphorylated by the conventional solid-phase method. A chemical phosphorylation is performed during the last step of automated oligonucleotide synthesis so that only the full- length oligonucleotides have a 5'-phosphate group. By this arrangement only phosphorylated (i.e. full-length) oligonucleotides can be ligated with other adjacent oligonucleotides during the following TDL step thereby conveniently eliminating oligonucleotides that are too short.

The second step known as template directed ligation (TDL) results in a new synthetic single-stranded DNA product, which is subsequently converted to a double-stranded fragment, amplified and selected from the wild type strand in the following third step by PCR selective amplification comprises the following procedures:

(a) Assembly of the adjacent chemically synthesized and phosphorylated oligonucleotides on the single-stranded partially homologous DNA template of the natural (wild type) gene allowing the oligonucleotides to anneal to the template in their proper order;

(b) Selection of the full-length oligonucleotides from a crude mixture of oligonucleotides after chemical DNA synthesis. Due to chemical phosphorylation only full-length oligonucleotides can be ligated with other assembled adjacent oligonucleotides, and therefore they are selected from a crude mixture. In case of an average oligonucleotide length between 100 and 120 nucleotides with a coupling efficiency around 98.0–98.5%, what is typically used, only 10–20% of oligonucleotides in crude mixture constitute the full-length DNA products which are included in the synthesis method. In the prior art, the full-length oligonucleotides must be purified from the crude mixture by laborious methods. However, in the TDL-PCR method this is not necessary, because uncompleted oligonucleotides cannot be ligated and, therefore, they are not amplified during the following PCR step. This selection of full-length oligonucleotides makes the TDL-PCR method according to the present invention considerably more advantageous over other known methods for a gene synthesis;

(c) Nick closing. Adjacent oligonucleotides assembled on the single-stranded wild- type DNA template are ligated together thereby closing nicks between adjacent oligonucleotides. Partially ligated DNA fragments can be completed in the following repeated rounds of the TDL step. Contrary to an exponential amplification in the ligase chain reaction (LCR), the amount of the final product is increased linearly during cycling in TDL step, if there is a sufficient excess of free oligonucleotides. Therefore, the yield depends on the ratio of template to oligonucleotides. The Pfu DNA ligase employed is extremely thermostable and possesses high nick-closing activity in contrast with low level of blunt ended (template-independent) ligation activity and therefore was used and is recommended for this application.

During the third and final step of the TDL-PCR method according to the present invention the newly assembled and sealed single-stranded DNA is converted to the double-stranded fragment and subsequently amplified and selected from the wild type template strand by the PCR with short flanking primers that are complementary only to the new synthetic strand. These flanking primers also contain sites for selected restriction enzymes in order to facilitate the cloning of an amplified DNA fragment.

The following example is provided to illustrate the practice of the invention and is not intended to limit the scope thereof.

EXAMPLE I

Synthesis of Bt toxin gene

In this example, the above-described TDL-PCR method was employed to synthesize a cryIC gene which encodes a *Bacillus thuringiensis* (Bt) endotoxin. The natural gene was found to be poorly expressed in transgenic plants. Efficient transcription of native cry genes in plant cell nuclei was achieved by the removal of AT-rich sequences that cause mRNA instability or aberrant splicing, and the translation of cry mRNAs was enhanced by modification of their codon usage to make it more similar to that of the host plant. In addition, the sequence context around translation start was modified to conform the eukaryotic consensus (Kozak, 1986).

Design of the Synthetic Gene

Design of the synthetic cryIC gene was based on the sequence of the corresponding wild-type gene (cryIСa5, as in FIG. 2) SEQ. ID NO:1. In fact, the cryICa5 sequence represents a consensus of all known cryIC genes and is identical in three *B. thuringiensis* strains K26-21, MR1-37 and sub sp.aizawai 7.29. Modifications of the synthetic cryIC gene (s-cryIC) sequence did not alter the amino acid sequence of the minimal toxic fragment of the Cry IC protoxin, containing N-terminal fragment with length of 630 amino acid residues (FIG. 2) SEQ. ID NO:2. To ensure proper transcription and translation of this synthetic gene in plants, 258 bp of the bacterial cryIC sequence (EMBL X96682; 1890 bp) were changed such that 249 out of 630 codons were modified according to preferential codon usage in alfalfa and other dicotyledonous plants. These nucleotide exchanges also removed 21 potential plant polyadenylation signals, 12 ATTTA motives, 68 sequence blocks with 6 or more consecutive A or T nucleotides, as well as all sequence motifs containing 5 or more G+C or A+T nucleotides. In addition, sequences around the translation initiation site were changed in order to conform the eukaryotic consensus sequence, and a TAG stop codon was introduced downstream of amino acid codon 630. The G+C content of the bacterial cryIC gene, was thus increased from 36.6% to 44.8% in the synthetic gene.

Oligonucleotide Synthesis

Oligonucleotides were synthesized with an Applied Biosystems 380B DNA synthesizer, using a 1000 Å controlled pore glass support (Millipore, Eschborn, Germany). Except for primers located at the 5'-termini of TDL-PCR sequence blocks (see below), the 5'-ends of oligonucleotides were chemically phosphorylated with 5'-Phosphate-ONphosphoramidite (Clontech, Heidelberg, Germany) according to manufacture's manual in the final step of DNA synthesis. The synthesis products were deprotected with ammonium hydroxide, desalted on NAP25 (Pharmacia, Freiburg, Germany) columns, and used for TDL-PCR without additional purification.

Gene Construction

The designed DNA sequence of the s-cryIC gene (FIG. 2) SEQ ID NO:1 was divided into three blocks separated by HincII and BglII cleavage sites. The BamHI-HincII block-I was constructed from eight, the HincII - BglII block-II from five, and the BglII-BamHI block-III from seven oligonucleotides. The oligonucleotides were assembled on a single-stranded DNA template of phagemid pR1, carrying the 630 N-terminal codons of the wild-type *B. thuringiensis* cryIC gene (FIGS. 1 and 2) SEQ ID NO:2. Terminal oligonucleotides in each TDL-PCR block carried unique sequences on their 5' and 3' ends, which were not complementary with the template, but were matched to short PCR primers for selective amplification of the synthetic DNA strand. These PCR primers contained unique restriction enzyme cleavage sites used for cloning of the amplified double-stranded DNA fragments into pBluescript. The TDL-PCR block-I was PCR amplified by a 5'-primer (5'-AAGAGGATCCACCATGGAGGAGAAC-3'), SEQ ID NO:3 carrying a BamHI site and a 3'-primer (5'-ATGATCTAGATGCAGTAGCG-3'). SEQ. ID NO:4 The 3'-primer was complementary to an oligonucleotide (5'-GTCAACTAACAAGGGAAGTTTATACG-GACCCACGCT ACTGCATCTAGATCAT-3') SEQ ID NO:5 at the 3'-end of block-I, that carried cryIC sequences with the HincII site, and unrelated overhang sequences with an XbaI site. The oligonucleotide at the 5'-end of block-II (5'-GATAACTCGAGCGAGCCTAAACTATGA-CAATAGGAGATATCCAATTCAG CCAGTTG-3') SEQ ID NO:6 added unique DNA sequences with an XhoI site to the cryIC sequences upstream of the HincII site and matched a PCR primer (5'-GATAACTCGAGCGAGCCTA-3') SEQ ID NO:7. The 3'-terminal oligonucleotide in block-II carried cryIC sequences extending to the BglII site and downstream overhang sequences with an XbaI site that were complementary to a PCR primer (5'-CCTGACTCTAGAAGATC-3'). SEQ ID NO:8 In the oligonucleotide located at the 5'-end of block-III an EcoRI site was added upstream to the BglII site of cryIC gene, fitting to a PCR primer (5'-CTGTCTGAATTCAAAGATC-3'). SEQ ID NO:9 The oligonucleotide at the 3'-end of block-III carried a BamHI site, following the position of TAG stop codon in the pR1 phagemid, as well as adjacent unique sequences with a NotI site that were complementary to a PCR primer (5'-AGCATGCGGCCGCGGATCC-3') SEQ ID NO:10.

TDL Technique

Template directed ligation (TDL) reactions were carried out at a template to oligonucleotide ratio 1:200 (a total of 0.05 pM of template versus 10 pM of each oligonucleotide) in a final volume of 50 μl using a reaction buffer (20 mM Tris.HCl (pH 7.5), 20 mM KCl, 10 mM $MgCl_2$ 0,1% NP-40, 0.5 mM rATP, 1 mM DTT)-and 4 U Pfu DNA ligase (Stratagene), or any other similar thermostable DNA ligase.

Thirty cycles of TDL reactions were used to obtain a desirable amount of a TDL product. The temperature range during melting step is between 90 to 98° C. with a preferable temperature of 92°, with 1 minute of required step time. Annealing and ligation were performed at a temperature range of 45 to 60° C. with a preferable temperature of 52° C. during required step time from 3 to 10 minutes. Melting step was followed by annealing and ligation step to obtain a TDL cycle which was repeated at least 30 times. To increase the number of TDL cycles for every additional 30 cycles a new portion of rATP (0.5 mM) and 4 U of Pfu ligase was added. Temperature cycling during TDL step was done on a Perkin-Elmer thermal cycler (Norwalk, Conn.).

PCR Selective Amplification of Synthetic TDL-PCR Blocks

5 μl from the TDL reaction mix served as template for PCR amplification with 100 pM of primers, 250 μM dNTP and 2.5 U Ampli-Taq or any other similar thermostable DNA polymerase such as UlTma (Perkin-Elmer) polymerase in 100 μl buffer (10 mM Tris.HCl (pH 9.0), 50 mM KCl and 0.1% Triton-X100), using of 30 cycles at 92° C. for 1 min, 45° C. for 1 min, and at 72° C. for 1.5 minutes, with final extension for 10 minutes, at 72° C. PCR amplifications were performed on a Perkin-Elmer (Norwalk, Conn.) thermal cycler. The amplified DNA fragments were gel purified, digested with BamHI-XbaI (block-I), XhoI-XbaI (block-II), and EcoRI-NotI (block-III), then cloned in pBluescript SK+ to verify their DNA sequences.

The synthetic cryIC gene coding for an N-terminal protoxin fragment of 630 amino acids was designed (FIG. 2) by exchanging 286 bp of the bacterial cryIC sequence (EMBL X96682; 1890 bp) such that 249 out of 630 codons were modified according to preferential codon usage in dicotyledonous plants. These exchanges removed 21 potential plant polyadenylation signals, 12 ATTTA motifs, 68 sequence blocks with 6 or more consecutive A/T's, and all motifs containing 5 or more G+C or A+T nucleotides. Sequences around the translation initiation site were changed to conform to the eukaryotic consensus sequence, and a TAG stop codon was introduced downstream of amino acid codon 630. The G+C content of the cryIC gene was thus increased from 36.6% to 44.8%. The s-cryIC gene was synthesized from oligonucleotides of 70–130 bases that were chemically phosphorylated at their 5'-ends. Since chemical phosphorylation is performed as the last step of automated DNA synthesis, only full-length oligonucleotides contain the 5'-phosphate group. Bacterial cryIC sequences coding for the 630 N-terminal codons were cloned in a pBluescript vector to generate a single- stranded DNA template for ordered annealing of 5–8 synthetic oligonucleotides by partial base-pairing. The adjacent oligonucleotides were assembled and ligated on this single- stranded template by a thermostable Pfu-ligase using 30–60 cycles of repeated melting, annealing and ligation. In combination with chemical phosphorylation this template directed ligation (TDL, FIG. 1) method provided a sequence specific selection for phosphorylated full-length oligonucleotides from a complex mixture of nonphosphorylated failure synthesis products, and yielded a linear amplification of single-stranded synthetic cryIC DNA segments generated by ligation. Therefore, except for desalting, no additional purifications of a crude oligonucleotide mixture after chemical DNA synthesis were necessary. The TDL ligation at high temperatures also circumvented potential problems of erroneous annealing. The synthetic cryIC sequences were converted to double-stranded DNA fragments and specifically amplified by PCR using short end-primers that did not anneal to the bacterial cryIC template carried by the pBluescript vector. The s-cryIC gene was thus synthesized from three sequence blocks that were combined by ligation of HincII and BglII digested DNA fragments, and cloned in pBluescript.

Figure 2A:
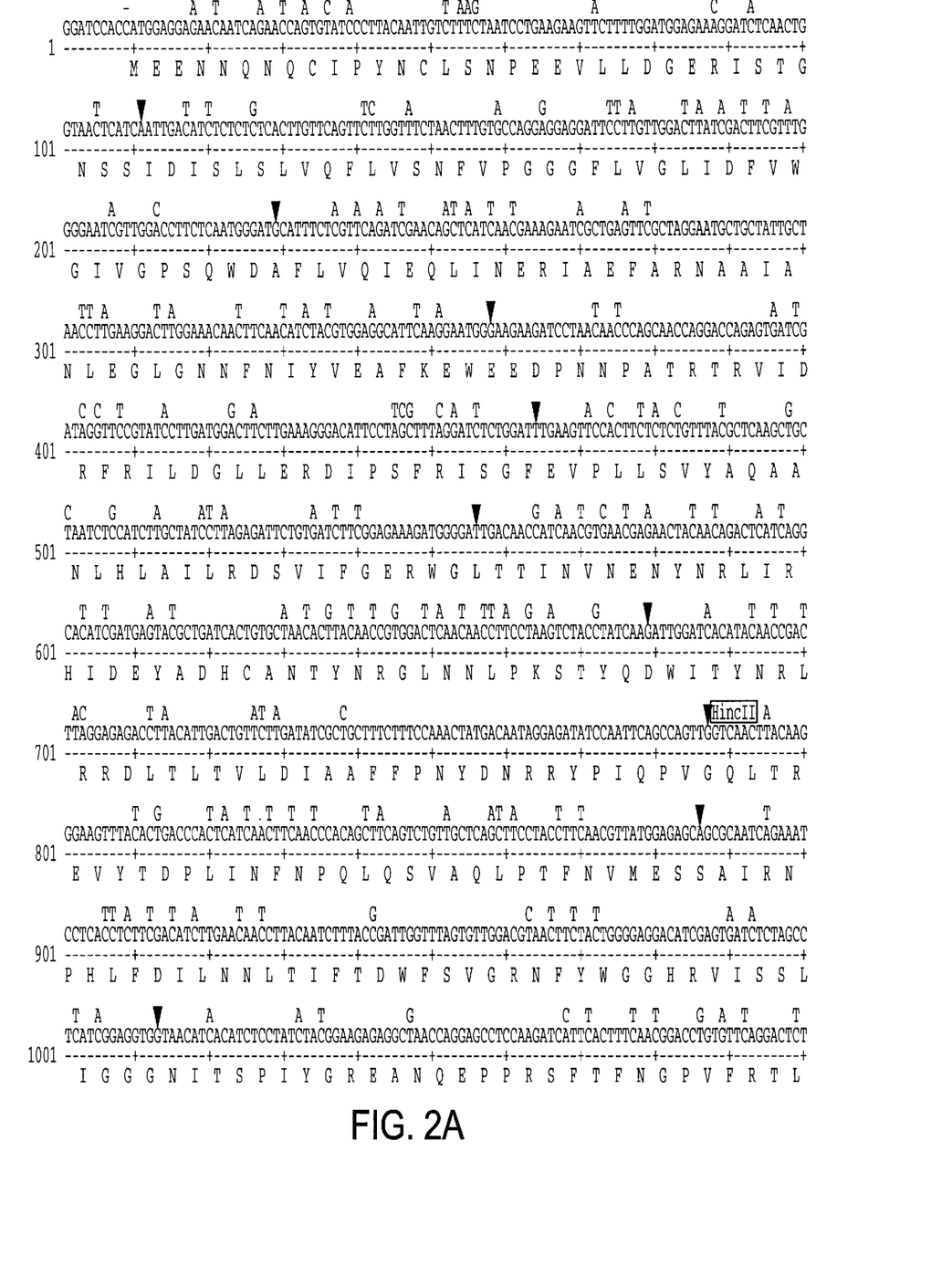
FIG. 2 shows the nucleotide sequence of the synthetic cryIC gene. Where different, the native (bacterial) sequence is shown above. The amino acid sequence is shown below.

With further reference to the Figures relating to this Example, FIG. 2 shows the nucleotide sequence of the synthetic cryIC gene (s-cryIC). Nucleotides of the bacterial cryIC sequence (b-cryIC) exchanged in the synthetic gene are shown in the upper lanes. The amino acid sequence of the truncated CryIC- endotoxin is displayed in single letter code below the s-cryIC sequence. The nucleotide sequence of the s-cryIC region coding for 630 codons starts with an ATG codon in a sequence context fitting the eukaryotic consensus and terminates at aTAG stop codon. Vertical black arrows above the s-cryIC sequence indicate the boundaries of adjacent synthetic oligonucleotides used for TDL-PCR gene synthesis. HincII and BglII cleavage sites used for the assembly of three TDL-PCR blocks are framed.

The errors (3 small deletions, 1 transversion and 1 transition) found in the TDL-PCR products were corrected by site-directed mutagenesis using a USE kit (Pharmacia) or by assembly of non-mutated restriction fragments.

Plant gene expression constructs and transformation of alfalfa and tobacco.

The plant expression vector pPCV91 was constructed by modification of pPCV720. A NotI site in the RK2-domain was eliminated by filling in with DNA polymerase Klenow fragment, and a CaMV35S promoter with four repeats of the enhanced domain (−90 to −418), was introduced into the HindIII site of pPCV720. Upstream of a BamHI cloning site this cassette contained 20 bp from the 3'-end of the untranslated Ω leader sequence of tobacco mosaic virus (TMV) RNA, whereas downstream of the BamHI site it carried a polyadenylation signal sequence derived from the CaMV 35S RNA gene. A BamHI site present in the mannopine synthase promoter(pmas) of pPCV720 was replaced by a NotI site using a Sau3A-NotI adaptor SEQ ID NO:11) (5'-GATCTGCGGCCGCA-3'). The resulting vector pPCV91 carried three plant gene expression cassettes with unique BamHI, NotI and SalI cloning sites. To construct pNS6, the synthetic cryIC gene was cloned as a BamHI fragment downstream of the CaMV35S promoter. In pNS7 a synthetic pat gene, coding for a phosphinothricine acetyltransferase (pat) gene and a chiAII gene from *Serratia marcescens* were inserted into the SalI and NotI sites located respectively downstream of the mas 1' and 2' promoters. A bacterial cryIC gene from *B. thuringinesis* subsp.. aizawai 7.29 (EMBL X96682), carrying the 756 N-terminal codons of cryIC, was cloned in pGIFI in which it replaced the synthetic cryIC gene of pNS7. Vectors pNS6, pNS7 and pGIF1 were conjugated to *Agrobacterium tumefacines* GV3101 (pMP90RK), and used for transformation of alfalfa (*Medicago sativa* L. var. Regen S clone RA3) and tobacco (*Nicotaina tabacum* SR) as described. To select for transformed explant, alfalfa and tobacco tissue culture media contained respectively 40 μg /ml and 15 μg/ml of hygromycin were used.

Monitoring the expression of CryIC in transgenic plants

Bacterial and synthetic cryIC genes, coding for the 630 N-terminal amino acids of the CryIC toxin (FIG. 2), were cloned into the BamHI site of a pAEN4 vector carrying the CaMV35S gene expression cassette of pPCV91. *Arabidopsis thaliana* protoplast were isolated from root cultures and transformed by PEG-mediated DNA uptake, using $1.5 \times 10^6$ protoplast and 35 μg plasmid DNA in each experiment. The protoplast were harvested 48 hours after DNA uptake and lysed in SDS-sample buffer to separate proteins on 10% SDS-PAGE before immunoblotting. An antibody used for immunoblotting was raised against a truncated CryIC δ-endotoxin carrying 756 N-terminal amino acids. Expression of CryIC in *E. coli* strains, carrying bacterial or synthetic cryIC genes respectively in pET-11a or 11d, was monitored-by a second alkaline phosphatase conjugated goat anti-rabbit antibody. Immunoblott analysis of proteins synthesized in plant cells was performed using an ECL kit (Amersham).

RNA (20 μg) samples isolated from leaves and petioles of alfalfa plants were separated on agarose-formaldehyde gels. BamHI fragments (1.9 kb), carrying either synthetic or bacterial cryIC sequences (FIG. 2), and a NotI fragment of the chiAII gene (1.8 kb) were labeled by random-priming and used as hybridization probes.

Insect bioassay

Leaf bioassay were performed with the Egyptian cotton leafworm (*Spodoptera littoralis*) and the beet armyworm (*Spodoptera exigua*) using neonate, 2–3rd, 3–4th, and 4–5–6th instar larvae. Ten larvae of selected developmental stage were placed on a moistened filter disc in Petri dishes with detached leaves from greenhouse grown plants. The assays were repeated 2–3 times for each plant. The mortality of neonate larvae was scored after 3 days, whereas the mortality of larvae from 2–4th and from 4–6th instar stages were evaluated respectively after 5 and 7 days. For the insect assays with whole plants, transgenic greenhouse grown alfalfa lines producing 0.02 to 0.1% of total soluble protein as CryIC and *S. exigua* larvae of the 3–4th instar stage were used. Three NS7 and three NS6 transgenic, as well as wild-type plants were infested with 15–20 larvae each. In "free-choice" experiments, 25 larvae were placed in a Petri dish located between transgenic NS6 or NS7 and nontransgenic alfalfa plants in the greenhouse. Leaf damage was evaluated after 6 days.

Further details regarding this example may be found in our co-pending application titled "Synthetic *Bacillus Thuringiensis* Gene Encoding an Insect Toxin".

Although only preferred embodiments are specifically described herein, it will be appreciated that many modifications and variations of the present invention are possible in light of the above teachings and within the purview of the appended claims without departing from the spirit and intended scope of the invention.

What is claimed is:

1. A method of constructing a synthetic single-stranded DNA molecule having an altered sequence relative to a template comprising:

(a) providing a single-stranded DNA template;

(b) chemically synthesizing a plurality of single-stranded oligonucleotides which are partially complementary to said template and form a contiguous sequence upon hybridization to said template, wherein mismatches between said oligonucleotides and said single-stranded template are located at any position internal to said oligonucleotides, and wherein the 5' end of any annealed oligonucleotide which is located at the junction point with another annealed oligonucleotide is phosphorylated; and (c) without any PCR amplification of said oligonucleotides, subjecting a mixture comprising said template, said oligonucleotides, and thermostable DNA ligase to repeated cycles of increased and lowered temperature to achieve repeated melting and annealing of DNA strands, whereby a synthetic single-stranded molecule DNA strand is produced by ligation of adjacent oligonucleotides.

2. A method of constructing a synthetic double-stranded DNA molecule having an altered sequence relative to a template comprising:

(a) providing a single-stranded DNA template;

(b) chemically synthesizing a plurality of single-stranded oligonucleotides which are partially complementary to said template and form a contiguous sequence upon hybridization to said template, wherein mismatches between said oligonucleotides and said single-stranded template are located at any position internal to said oligonucleotides, and wherein the 5' end of any annealed oligonucleotide which is located at the junction point with another annealed oligonucleotide is phosphorylated;

(c) without any PCR amplification of said oligonucleotides, subjecting a mixture comprising said template, said oligonucleotides, and thermostable DNA ligase to repeated cycles of increased and lowered temperature to achieve repeated melting and annealing of DNA strands, whereby a synthetic single-stranded molecule DNA strand is produced by ligation of adjacent oligonucleotides;

(d) producing an oligonucleotide primer complementary only to said synthetic DNA strand; and (e) subjecting a mixture comprising said synthetic DNA strand, said primer, and thermostable DNA polymerase to repeated cycles of increased and lowered temperature to achieve repeated melting and annealing of DNA strands, whereby a double-stranded DNA molecule is produced.

3. A method of constructing a synthetic double-stranded DNA molecule having an altered sequence relative to a template comprising:

(a) providing a single-stranded DNA template;

(b) chemically synthesizing a plurality of single-stranded oligonucleotides which are partially complementary to said template and form a contiguous sequence upon hybridization to said template, wherein mismatches between said oligonucleotides and said single-stranded template are located at any position internal to said oligonucleotides, and wherein the 5' end of any annealed oligonucleotide which is located at the junction point with another annealed oligonucleotide is phosphorylated;

(c) without any PCR amplification of said oligonucleotides, subjecting a mixture comprising said template, said oligonucleotides, and thermostable DNA ligase to repeated cycles of increased and lowered temperature to achieve repeated melting and annealing of DNA strands, whereby a synthetic single-stranded molecule DNA strand is produced by ligation of adjacent oligonucleotides;

(d) producing oligonucleotide primers which in PCR reactions only amplify the synthetic DNA strand; and (e) subjecting a mixture comprising said synthetic DNA strand, said primers, and thermostable DNA polymerase to repeated cycles of increased and lowered temperature to achieve repeated melting and annealing of DNA strands, whereby a double-stranded DNA molecule is produced.

4. The method of claims 1, 2 or 3 wherein said oligonucleotides are produced by synthesis on a automated DNA synthesizer.

5. The method of claim 4 wherein said oligonucleotides which are phosphorylated at their 5' end are the result of a phosphorylation step on the DNA synthesizer, said phosphorylation occurring at the end of synthesis of said oligonucleotide.

6. The method of claims 1, 2 or 3 wherein said thermostable DNA ligase is Pfu.

7. The method of claim 3 wherein at least one of said oligonucleotide primers for a PCR reaction is further designed to create a restriction enzyme site in the PCR product.

8. The method of claim 2 or 3 wherein said synthetic double-stranded DNA molecule comprises a *Bacillus thuringiensis* toxin gene.

* * * * *

```
                          SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH:  1907 base pair
         (B) TYPE:  nucleic acid
         (C) STRANDEDNESS:  double
         (D) TOPOLOGY:  linear (ii) MOLECULE TYPE:  other nucleic acid
         (A) DESCRIPTION:  artificial DNA, synthetic gene (iii) HYPOTHETICAL:  no (iv) ANTI-SENSE:  no (v) ORIGINAL SOURCE:
         (A) ORGANISM:  artificial DNA
         (B) STRAIN:  not applicable
         (C) INDIVIDUAL ISOLATE:  not applicable
         (D) DEVELOPMENTAL STAGE:  not applicable
         (E) HAPLOTYPE:  not applicable
         (F) TISSUE TYPE:  not applicable
         (G) CELL TYPE:  not applicable
         (H) CELL LINE:  not applicable
         (I) ORGANELLE:  not applicable (vii) IMMEDIATE SOURCE:
         (A) LIBRARY:  not applicable
         (B) CLONE:  plant expression construct PNS6

(viii) POSITION IN GENOME:  not applicable (ix) FEATURE:
         (A) NAME/KEY:  SEQ. ID NO. 1 is the sequence in claim 1, and
             relevant residues starting from 1 to 1907
         (B) LOCATION:  not available
         (C) IDENTIFICATION METHOD:  experiment in specification
         (D) OTHER INFORMATION:  not applicable (x) PUBLICATION INFORMATION:
         (A) AUTHORS:  Strizhov, Nicolai; Keller, Menachem; Mathur,
             Jadeep; Koncz-K lm n, Zsuzsanna; Bosch, Dirk; Prudovsky,
             Evgenia; Schell, Jeff; Sneh, Baruch; Koncz, Csaba;
             Zilberstein, Aviah
         (B) TITLE: A synthetic cryIC gene, encoding a Bacillus
             thuringiensis k-endotoxin, confers Spodoptera resistance
             in alfalfa and tobacco
         (C) JOURNAL: Proc. Natl. Acad. Sci. USA
         (D) VOLUME:  93
         (E) ISSUE:  26
         (F) PAGES:  15012 - 15017
         (G) DATE:  24 - DEC - 1996
         (K) RELEVANT RESIDUES IN SEQ ID NO:1 FROM 1 TO 1907
```

(xii) SEQUENCE DESCRIPTION: SEQ ID NO:1:

```
GGATCCACC ATG GAG GAG AAC AAT CAG AAC CAG TGT ATC CCT TAC AAT TGT CTT    54
          Met Glu Glu Asn Asn Gln Asn Gln Cys Ile Pro Tyr Asn Cys Leu
                        5                  10                      15

TCT AAT CCT GAA GAA GTT CTT TTG GAT GGA GAA AGG ATC TCA ACT GGT         102
Ser Asn Pro Glu Glu Val Leu Leu Asp Gly Glu Arg Ile Ser Thr Gly
                20              25                  30

AAC TCA TCA ATT GAC ATC TCT CTC TCA CTT GTT CAG TTC TTG GTT TCT         150
Asn Ser Ser Ile Asp Ile Ser Leu Ser Leu Val Gln Phe Leu Val Ser
                35              40                  45

AAC TTT GTG CCA GGA GGA GGA TTC CTT GTT GGA CTT ATC GAC TTC GTT         198
Asn Phe Val Pro Gly Gly Gly Phe Leu Val Gly Leu Ile Asp Phe Val
            50              55                  60

TGG GGA ATC GTT GGA CCT TCT CAA TGG GAT GCA TTT CTC GTT CAG ATC         246
Trp Gly Ile Val Gly Pro Ser Gln Trp Asp Ala Phe Leu Val Gln Ile
        65              70              75

GAA CAG CTC ATC AAC GAA AGA ATC GCT GAG TTC GCT AGG AAT GCT GCT         294
Glu Gln Leu Ile Asn Glu Arg Ile Ala Glu Phe Ala Arg Asn Ala Ala
80              85              90                      95

ATT GCT AAC CTT GAA GGA CTT GGA AAC AAC TTC AAC ATC TAC GTG GAG         342
Ile Ala Asn Leu Glu Gly Leu Gly Asn Asn Phe Asn Ile Tyr Val Glu
                    100             105                 110

GCA TTC AAG GAA TGG GAA GAA GAT CCT AAC AAC CCA GCA ACC AGG ACC         390
Ala Phe Lys Glu Trp Glu Glu Asp Pro Asn Asn Pro Ala Thr Arg Thr
                115                 120                 125

AGA GTG ATC GAT AGG TTC CGT ATC CTT GAT GGA CTT CTT GAA AGG GAC         438
Arg Val Ile Asp Arg Phe Arg Ile Leu Asp Gly Leu Leu Glu Arg Asp
            130                 135                 140

ATT CCT AGC TTT AGG ATC TCT GGA TTT GAA GTT CCA CTT CTC TCT GTT         486
Ile Pro Ser Phe Arg Ile Ser Gly Phe Glu Val Pro Leu Leu Ser Val
145             150                 155

TAC GCT CAA GCT GCT AAT CTC CAT CTT GCT ATC CTT AGA GAT TCT GTG         534
Tyr Ala Gln Ala Ala Asn Leu His Leu Ala Ile Leu Arg Asp Ser Val
160                 165                 170                 175

ATC TTC GGA GAA AGA TGG GGA TTG ACA ACC ATC AAC GTG AAC GAG AAC         582
Ile Phe Gly Glu Arg Trp Gly Leu Thr Thr Ile Asn Val Asn Glu Asn
                180                 185                 190

TAC AAC AGA CTC ATC AGG CAC ATC GAT GAG TAC GCT GAT CAC TGT GCT         630
Tyr Asn Arg Leu Ile Arg Hic Ile Asp Glu Tyr Ala Asp His Cys Ala
                195                 200                 205

AAC ACT TAC AAC CGT GGA CTC AAC AAC CTT CCT AAG TCT ACC TAT CAA         678
Asn Thr Tyr Asn Arg Gly Leu Asn Asn Leu Pro Lys Ser Thr Tyr Gln
            210                 215                 220

GAT TGG ATC ACA TAC AAC CGA CTT AGG AGA GAC CTT ACA TTG ACT GTT         726
Asp Trp Ile Thr Tyr Asn Arg Leu Arg Arg Asp Leu Thr Leu Thr Val
225                 230                 235

CTT GAT ATC GCT GCT TTC TTT CCA AAC TAT GAC AAT AGG AGA TAT CCA         774
Leu Asp Ile Ala Ala Phe Phe Pro Asn Tyr Asp Asn Arg Arg Tyr Pro
240                 245                 250                 255

ATT CAG CCA GTT GGT CAA CTT ACA AGG GAA GTT TAC ACT GAC CCA CTC         822
Ile Gln Pro Val Gly Gln Leu Thr Arg Glu Val Tyr Thr Asp Pro Leu
                260                 265                 270

ATC AAC TTC AAC CCA CAG CTT CAG TCT GTT GCT CAG CTT CCT ACC TTC         870
Ile Asn Phe Asn Pro Gln Leu Gln Ser Val Ala Gln Leu Pro Thr Phe
                275                 280                 285

AAC GTT ATG GAG AGC AGC GCA ATC AGA AAT CCT CAC CTC TTC GAC ATC         918
Asn Val Met Glu Ser Ser Ala Ile Arg Asn Pro His Leu Phe Asp Ile
            290                 295                 300

TTG AAC AAC CTT ACA ATC TTT ACC GAT TGG TTT AGT GTT GGA CGT AAC         966
```

-continued

```
Leu Asn Asn Leu Thr Ile Phe Thr Asp Trp Phe Ser Val Gly Arg Asn
    305                 310                 315

TTC TAC TGG GGA GGA CAT CGA GTG ATC TCT AGC CTC ATC GGA GGT GGT        1014
Phe Tyr Trp Gly Gly His Arg Val Ile Ser Ser Leu Ile Gly Gly Gly
320                 325                 330                 335

AAC ATC ACA TCT CCT ATC TAC GGA AGA GAG GCT AAC CAG GAG CCT CCA        1062
Asn Ile Thr Ser Pro Ile Tyr Gly Arg Glu Ala Asn Gln Glu Pro Pro
                340                 345                 350

AGA TCA TTC ACT TTC AAC GGA CCT GTG TTC AGG ACT CTT TCA AAT CCT        1110
Arg Ser Phe Thr Phe Asn Gly Pro Val Phe Arg Thr Leu Ser Asn Pro
        355                 360                 365

ACT CTT CGA CTT CTT CAG CAA CCT TGG CCA GCT CCA CCA TTC AAC CTT        1158
Thr Leu Arg Leu Leu Gln Gln Pro Trp Pro Ala Pro Pro Phe Asn Leu
    370                 375                 380

CGT GGT GTT GAA GGA GTT GAG TTC TCT ACA CCT ACA AAC AGC TTC ACC        1206
Arg Gly Val Glu Gly Val Glu Phe Ser Thr Pro Thr Asn Ser Phe Thr
385                 390                 395

TAT CGT GGA AGA GGT ACT GTT GAT TCT CTT ACT GAA CTT CCA CCT GAG        1254
Tyr Arg Gly Arg Gly Thr Val Asp Ser Leu Thr Glu Leu Pro Pro Glu
400                 405                 410                 415

GAC AAC AGT GTG CCA CCT CGT GAA GGA TAC AGT CAT CGT CTT TGT CAT        1302
Asp Asn Ser Val Pro Pro Arg Glu Gly Tyr Ser His Arg Leu Cys His
                420                 425                 430

GCA ACC TTC GTT CAA AGA TCT GGA ACA CCT TTC CTT ACA ACT GGT GTT        1350
Ala Thr Phe Val Gln Arg Ser Gly Thr Pro Phe Leu Thr Thr Gly Val
        435                 440                 445

GTG TTC TCT TGG ACT CAT CGT AGT GCA ACT CTT ACC AAC ACA ATT GAT        1398
Val Phe Ser Trp Thr His Arg Ser Ala Thr Leu Thr Asn Thr Ile Asp
    450                 455                 460

CCA GAG AGG ATC AAC CAG ATC CCT CTT GTG AAA GCA TTC AGA GTT TGG        1446
Pro Glu Arg Ile Asn Gln Ile Pro Leu Val Lys Gly Phe Arg Val Trp
465                 470                 475

GGA GGA ACC TCT GTG ATT ACA GGA CCA GGA TTC ACA GGA GGT GAT ATC        1494
Gly Gly Thr Ser Val Ile Thr Gly Pro Gly Phe Thr Gly Gly Asp Ile
480                 485                 490                 495

CTT CGA AGA AAC ACC TTT GGT GAC TTC GTT TCT CTT CAA GTG AAC ATC        1542
Leu Arg Arg Asn Thr Phe Gly Asp Phe Val Ser Leu Gln Val Asn Ile
                500                 505                 510

AAC TCA CCA ATC ACC CAA AGA TAC CGT CTT AGA TTT CGT TAC GCT TCT        1590
Asn Ser Pro Ile Thr Gln Arg Tyr Arg Leu Arg Phe Arg Tyr Ala Ser
        515                 520                 525

AGT AGG GAT GCA CGA GTT ATC GTT CTT ACA GGA GCT GCA TCT ACA GGA        1638
Ser Arg Asp Ala Arg Val Ile Val Leu Thr Gly Ala Ala Ser Thr Gly
    530                 535                 540

GTG GGA GGT CAA GTT AGT GTG AAC ATG CCT CTT CAG AAA ACT ATG GAG        1686
Val Gly Gly Gln Val Ser Val Asn Met Pro Leu Gln Lys Thr Met Glu
545                 550                 555

ATC GGA GAG AAC CTC ACA TCT AGA ACA TTC AGA TAC ACC GAC TTC AGT        1734
Ile Gly Glu Asn Leu Thr Ser Arg Thr Phe Arg Tyr Thr Asp Phe Ser
560                 565                 570                 575

AAT CCT TTC TCA TTC AGA GCT AAT CCA GAC ATC ATC GGT ATC AGT GAA        1782
Asn Pro Phe Ser Phe Arg Ala Asn Pro Asp Ile Ile Gly Ile Ser Glu
                580                 585                 590

CAA CCT CTC TTC GGT GCA GGT TCT ATC AGT AGC GGT GAA CTT TAC ATC        1830
Gln Pro Leu Phe Gly Ala Gly Ser Ile Ser Ser Gly Glu Leu Tyr Ile
        595                 600                 605

GAC AAG ATC GAG ATC ATC CTT GCA GAT GCA ACA TTT GAA GCA GAA TCT        1878
Asp Lys Ile Glu Ile Ile Leu Ala Asp Ala Thr Phe Glu Ala Glu Ser
    610                 615                 620
```

```
GAC CTT GAA AGA GCA CAA AAG TAG GAT CC                                    1907
Asp Leu Glu Arg Ala Gln Lys End
    625                 630
```

(2) INFORMATION FOR SEQ ID NO: 2:

(i) SEQUENCE CHARACTERISTICS:
        (A) LENGTH:  630 amino acid residues
        (B) TYPE: amino acid
        (D) TOPOLOGY: linear    (ii) MOLECULE TYPE:
        (A) DESCRIPTION:  truncated protein   (iii) HYPOTHETICAL:  no    (iv) ANTI-SENSE:  no     (v) FRAGMENT TYPE: N-terminal fragment    (vi) ORIGINAL SOURCE:
        (A) ORGANISM:  Bacillus thuringiensis
        (B) STRAIN:  K26-21, MR1-37, subsp. aizawai 7.29
        (C) INDIVIDUAL ISOLATE:  not applicable
        (E) HAPLOTYPE:  not applicable
        (F) TISSUE TYPE:  not applicable
        (G) CELL TYPE:  unicellular organism   (vii) IMMEDIATE SOURCE:  strains K26-21, MR1-37, subsp. aizawai
           7.29
        (A) LIBRARY:  not applicable
        (B) CLONE:  not applicable  (viii) POSITION IN GENOME:  not applicable
        (A) CHROMOSOME/SEGMENT:  not applicable
        (B) MAP POSITION:  not applicable
        (C) UNITS:  not applicable    (ix) FEATURE:  insecticidal control protein
        (A) NAME/KEY:  SEQ. ID NO: 2 : is the sequence in claim 6, and
           relevant residues from 1 to 630
        (B) LOCATION:  not available
        (C) IDENTIFICATION METHOD:  by experiment
        (D) OTHER INFORMATION:  specifically toxic to insects of
           spodoptera genus confers Spodoptera resistance being
           expressed in transgenic plants     (x) PUBLICATION INFORMATION:
        (A) AUTHORS:  Strizhov, Nicolai; Keller, Menachem; Mathur,
           Jadeep; Koncz-K lm n, Zsuzsanna; Bosch, Dirk; Prudovsky,
           Evgenia; Schell, Jeff; Sneh, Baruch; Koncz, Csaba;
           Zilberstein, Aviah
        (B) TITLE:  A synthetic cryIC gene, encoding a Bacillus
           thuringiensis k-endotoxin, confers Spodoptera resistance
           in alfalfa and tobacco
        (C) JOURNAL:   Proc. Natl. Acad. Sci. USA
        (D) VOLUME:  93
        (E) ISSUE:  26
        (F) PAGES:  15012 - 15017
        (G) DATE:  24 - DEC - 1996
        (K) RELEVANT RESIDUES IN SEQ ID NO: 2: FROM 1 TO 630

(xi) SEQUENCE DESCRIPTION: SEQ   ID NO:2:

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80
```

```
Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
        130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
                180                 185                 190

Asn Arg Leu Ile Arg His Ile Asp Glu Tyr Ala Asp His Cys Ala Asn
                195                 200                 205

Thr Tyr Asn Arg Gly Leu Asn Asn Leu Pro Lys Ser Thr Tyr Gln Asp
        210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
                260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
        290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
                340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
        370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
                420                 425                 430

Thr Phe Val Gln Arg Ser Gly Thr Pro Phe Leu Thr Thr Gly Val Val
            435                 440                 445

Phe Ser Trp Thr His Arg Ser Ala Thr Leu Thr Asn Thr Ile Asp Pro
450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495
```

```
Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
            515                 520                 525

Arg Asp Ala Arg Val Ile Val Leu Thr Gly Ala Ala Ser Thr Gly Val
            530                 535                 540

Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
            565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
            595                 600                 605

Lys Ile Glu Ile Ile Leu Ala Asp Ala Thr Phe Glu Ala Glu Ser Asp
            610                 615                 620

Leu Glu Arg Ala Gln Lys
625                 630
```

(2) INFORMATION FOR SEQ ID NO:3:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: 5'-primer     (xi) SEQUENCE DESCRIPTION: SEQ ID NO:3:

AAGAGGATCC ACCATGGAGG AGAAC                                      25

(2) INFORMATION FOR SEQ ID NO:4:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: 3'-primer     (xi) SEQUENCE DESCRIPTION: SEQ ID NO:4:

ATGATCTAGA TGCAGTAGCG                                            20

(2) INFORMATION FOR SEQ ID NO:5:

(i) SEQUENCE CHARACTERISTICS:
        (A) LENGTH: 52 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: cryIC block-I     (xi) SEQUENCE DESCRIPTION: SEQ ID NO:5:

```
GTCAACTAAC AAGGGAAGTT TATACGGACC CACGCTACTG CATCTAGATC AT            52
```

(2) INFORMATION FOR SEQ ID NO:6:

(i) SEQUENCE CHARACTERISTICS:
        (A) LENGTH: 56 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: cryIC block-II     (xi) SEQUENCE DESCRIPTION: SEQ ID NO:6:

```
GATAACTCGA GCGAGCCTAA ACTATGACAA TAGGAGATAT CCAATTCAGC CAGTTG        56
```

(2) INFORMATION FOR SEQ ID NO:7:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: primer     (xi) SEQUENCE DESCRIPTION: SEQ ID NO:7:

```
GATAACTCGA GCGAGCCTA                                                 19
```

(2) INFORMATION FOR SEQ ID NO:8:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: primer     (xi) SEQUENCE DESCRIPTION: SEQ ID NO:8:

```
CCTGACTCTA GAAGATC                                                   17
```

(2) INFORMATION FOR SEQ ID NO:9:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear     (ii) MOLECULE TYPE: oligonucleotide     (ix) FEATURE:
        (A) NAME/KEY: primer     (xi) SEQUENCE DESCRIPTION: SEQ ID NO:9:

```
CTGTCTGAAT TCAAAGATC                                                 19
```

(2) INFORMATION FOR SEQ ID NO:10:

(i) SEQUENCE CHARACTERISTICS:
        (A) LENGTH: 19 nucleotides

```
            (B) TYPE:  nucleic acid
            (C) STRANDEDNESS:  single
            (D) TOPOLOGY:  linear (ii) MOLECULE TYPE:  oligonucleotide (ix) FEATURE:
            (A) NAME/KEY:  primer (xi) SEQUENCE DESCRIPTION:  SEQ ID NO:10:

AGCATGCGGC CGCGGATCC                                                  19

(2) INFORMATION FOR SEQ ID NO:11:

(i) SEQUENCE CHARACTERISTICS:
            (A) LENGTH:  14 nucleotides
            (B) TYPE:  nucleic acid
            (C) STRANDEDNESS:  single
            (D) TOPOLOGY:  linear (ii) MOLECULE TYPE:  oligonucleotide (ix) FEATURE:
            (A) NAME/KEY:  adapter (xi) SEQUENCE DESCRIPTION:  SEQ ID NO:11:

GATCTGCGGC CGCA                                                       14
```